(12) United States Patent
Choi

(10) Patent No.: US 10,799,729 B2
(45) Date of Patent: Oct. 13, 2020

(54) PORTABLE AIR PURIFIER

(71) Applicant: Yeon-Ok Choi, Seoul (KR)

(72) Inventor: Yeon-Ok Choi, Seoul (KR)

( * ) Notice: Subject to any disclaimer, the term of this patent is extended or adjusted under 35 U.S.C. 154(b) by 332 days.

(21) Appl. No.: 15/597,287

(22) Filed: May 17, 2017

(65) Prior Publication Data

US 2018/0015310 A1 Jan. 18, 2018

(30) Foreign Application Priority Data

Jul. 15, 2016 (KR) .......................... 10-2016-0090154

(51) Int. Cl.
*A62B 23/02* (2006.01)
*F24F 3/16* (2006.01)
(Continued)

(52) U.S. Cl.
CPC ........... *A62B 23/02* (2013.01); *A61M 16/107* (2014.02); *A61M 16/16* (2013.01); *A62B 7/02* (2013.01);
(Continued)

(58) Field of Classification Search
CPC .. A62B 23/02; A62B 7/10; A62B 7/02; A62B 9/003; A62B 9/06; A62B 25/00; A61M 16/0063; A61M 16/107; A61M 16/16; A61M 16/1045; A61M 16/0666; A61M 2205/7536; A61M 2205/7545; A61M 2205/8206; A61M 16/0057; A61M 16/0066; A61M 16/10; A61M 16/105; A61M 16/1095; F24F 2006/008; F24F 2300/1617; F24F 2003/1642;
(Continued)

(56) References Cited

U.S. PATENT DOCUMENTS 1,170,526 A * 2/1916 Wallace ................. F24F 3/1411
  96/118
1,196,539 A * 8/1916 Goldberg .............. A61M 16/16
  128/200.11
(Continued)

FOREIGN PATENT DOCUMENTS

CN     203771568 U * 8/2014
JP     2011-110112 A    6/2011
(Continued)

*Primary Examiner* — Kathryn E Ditmer
(74) *Attorney, Agent, or Firm* — KORUS Patent, LLC; Seong Il Jeong

(57) ABSTRACT

Provided herein is a portable air purifier. The portable air purifier includes: a body; first to third accommodation portions configured to have respective open top surfaces in order to separately accommodate a battery, an air compressor, and water; first to third covers configured to selectively open and close the respective open top surfaces of the first to third accommodation portions; an air inlet connected to the lower portion of the second accommodation portion, and configured to accommodate a pre-filter; a siphon pipe positioned upright inside the water of the third accommodation portion, and configured such that the top thereof is connected to the air outlet of the air compressor; a cannula installed on the top of the third accommodation portion, and configured to supply purified, humidified air to a user; and a power switch configured to control the amount of air to be supplied.

3 Claims, 3 Drawing Sheets

(51) Int. Cl.
*A61M 16/16* (2006.01)
*A61M 16/10* (2006.01)
*A62B 7/02* (2006.01)
*A62B 7/10* (2006.01)
*A62B 9/00* (2006.01)
*A62B 9/06* (2006.01)
*A62B 25/00* (2006.01)
*B01D 47/02* (2006.01)
*B01D 50/00* (2006.01)
*B01F 3/04* (2006.01)
*B01F 15/00* (2006.01)
*A61M 16/00* (2006.01)
*A61M 16/06* (2006.01)

(52) U.S. Cl.
CPC ............... *A62B 7/10* (2013.01); *A62B 9/003* (2013.01); *A62B 9/06* (2013.01); *A62B 25/00* (2013.01); *B01D 47/021* (2013.01); *B01D 50/006* (2013.01); *B01F 3/04241* (2013.01); *B01F 15/00974* (2013.01); *F24F 3/1603* (2013.01); *A61M 16/0063* (2014.02); *A61M 16/0666* (2013.01); *A61M 2205/7536* (2013.01); *A61M 2205/7545* (2013.01); *A61M 2205/8206* (2013.01); *B01F 2003/04872* (2013.01); *B01F 2215/0091* (2013.01); *F24F 2003/1617* (2013.01); *F24F 2003/1642* (2013.01); *F24F 2003/1657* (2013.01); *F24F 2221/12* (2013.01); *Y02A 50/21* (2018.01)

(58) Field of Classification Search
CPC .. F24F 2221/12; F24F 2203/1024; F24F 6/00; F24F 6/02; F24F 2003/1617; B01D 47/021; B01D 50/006; B01D 50/00; B01D 47/02; B01F 3/04241; B01F 15/00974; B01F 2003/04872; B01F 2215/0091; B01F 3/04262; B01F 3/04269; B01F 2003/04865; Y02A 50/21; Y02A 50/20; A01K 63/042
USPC ........................................ 128/205.29, 205.12
See application file for complete search history.

(56) References Cited

U.S. PATENT DOCUMENTS

| | | | | |
|---|---|---|---|---|
| 2,088,720 A * | 8/1937 | Poliniak | ............... | A62B 7/10 128/200.13 |
| 2,153,227 A * | 4/1939 | Allstatter | ............... | G09F 3/04 40/668 |
| 2,960,321 A * | 11/1960 | Stoots, Jr. | ............ | A01K 63/042 261/30 |
| 3,216,650 A * | 11/1965 | Thyreen | ............... | A01K 63/042 417/234 |
| 3,217,444 A * | 11/1965 | Jeral | ...................... | A01K 97/05 43/57 |
| 3,265,067 A * | 8/1966 | Ehlinger | ............... | A61M 16/16 128/200.13 |
| 3,980,080 A * | 9/1976 | Muto | .................... | A62B 19/00 128/200.13 |
| 4,500,480 A * | 2/1985 | Cambio, Jr. | ........ | A61M 16/164 128/200.11 |
| 4,615,137 A * | 10/1986 | Radmanovich | ........ | A01K 97/05 261/121.2 |
| 4,899,740 A * | 2/1990 | Napolitano | .......... | A62B 18/003 116/268 |
| 5,065,753 A * | 11/1991 | Kalishman | ............ | A61M 16/16 128/200.11 |
| 5,078,759 A * | 1/1992 | Kira | ..................... | B01D 47/021 261/121.1 |
| 5,231,789 A * | 8/1993 | Radmanovich | ........ | A01K 97/05 261/121.2 |
| 5,634,291 A * | 6/1997 | Pham | .................... | A01K 97/05 43/56 |
| 6,799,573 B1 * | 10/2004 | Bonner | .................. | A62B 23/02 128/200.11 |
| 7,404,401 B1 * | 7/2008 | Brady | ..................... | A62B 7/10 128/205.27 |
| 2003/0079741 A1 * | 5/2003 | Sawka | ............. | A61M 16/0666 128/200.11 |
| 2003/0214056 A1 * | 11/2003 | Salter | .................... | A61M 16/16 261/124 |
| 2006/0174881 A1 * | 8/2006 | Jagger | .................. | A61M 16/10 128/201.25 |
| 2007/0175473 A1 * | 8/2007 | Lewis | .................. | A61J 11/0005 128/204.18 |
| 2010/0263672 A1 * | 10/2010 | Acharya | .................. | A62B 7/10 128/206.11 |
| 2011/0056496 A1 * | 3/2011 | Tilley | ...................... | A62B 7/10 128/205.27 |
| 2011/0126828 A1 * | 6/2011 | Wu | ......................... | A62B 7/10 128/201.25 |
| 2012/0018910 A1 * | 1/2012 | Moreno | ................ | A61M 16/16 261/122.1 |
| 2015/0000670 A1 * | 1/2015 | Kim | ........................ | A62B 7/10 128/206.11 |
| 2017/0106333 A1 * | 4/2017 | Zhu | .................... | B01D 53/1493 |
| 2017/0246486 A1 * | 8/2017 | Cazier | .................... | A62B 27/00 |

FOREIGN PATENT DOCUMENTS

| KR | 20-0273346 Y1 | 4/2002 |
|---|---|---|
| KR | 10-0766491 B1 | 10/2007 |
| KR | 10-1195175 B1 | 10/2012 |

* cited by examiner

PORTABLE AIR PURIFIER

BACKGROUND

1. Technical Field

The present invention relates generally to a suction-type portable air purifier, and more particularly to a portable air purifier that enables a user to inhale humidified air, purified using water, while conveniently carrying the portable air purifier regardless of place.

2. Description of the Related Art

Generally, as standards of living are increasing and a five-day work week system is actively being introduced, the leisure activities of people are expanding. These activities lead to increases in outdoor activities, such as mountain hiking, sports, meetings of people interested in the same subjects, etc. Furthermore, with the boom of wellness throughout society, health consciousness is on the rise, and thus the demand for a healthy environment is increasing.

There are many cases where an outdoor atmospheric environment is not healthy due to spring's yellow dust, pollen, automobile exhaust fumes, etc. The interiors of general old buildings are exposed to harmful materials, such as microbes, for example, fungi, asbestos, etc., and thus the number of asthma or allergy sufferers is increasing.

In particular, respiratory dust is fine dust (PM 10) having a particle size less than 10 μm. Such particles cannot be blocked even when a general yellow dust mask is used. The fine particles of respiratory dust less than 2.5 μm are dust that may infiltrate deep into the lung, and are dust (approximately in the range of 0.5 to 5 μm) that may cause pneumoconiosis.

Accordingly, there is a tendency for separate expensive air purifiers to become essential home and office appliances.

However, air purifiers are problematic in that it is difficult to carry them because they are manufactured in large sizes and in that the manufacturing costs thereof are expensive because they are manufactured in large sizes and thus the sizes of the parts thereof are large.

In order to overcome these problems, Korean Registered Utility Model No. 0273346 (registered on Apr. 12, 2002) discloses a portable compact air purifier that purifies air, introduced via an air blower, by means of a plurality of filters having various functions, thereby enabling a user to inhale the purified air. The portable compact air purifier includes: an upper ventilation part including a ventilation hole, a communication adjustment rotation plate, and an adjustment rotation plate grip; an intermediate air purifying space including an air purification filter unit, an ion generator, and an external air communication hole; and a lower machine part including an air blower, and an external air suction hole.

However, the conventional portable compact air purifier configured as described above is configured to purify air by means of a plurality of air purification filter units each including a contaminant elimination filter, an antibacterial filter, and a fine dust filter. The conventional portable compact air purifier is problematic in that due to the non-use of water, it is difficult to filter out ultra-fine dust and a humidification effect cannot be expected and in that high maintenance costs are required for the periodic replacement of a specific company's special filter unit. Furthermore, the conventional portable compact air purifier is also problematic in that the structure of the ion generator is complex due to the components thereof, such as an air blower, and it is difficult to carry the conventional portable compact air purifier for a long period of time due to high power consumption.

SUMMARY

The present invention has been conceived to overcome the above-described problems, and an object of the present invention is to provide a portable air purifier that can eliminate maintenance costs required for the periodic replacement of a special filter unit, can reduce manufacturing costs by minimizing internal components and thus reducing the volume of the portable air purifier, and can facilitate the carrying of the portable air purifier.

According to an aspect of the present invention, there is provided a portable air purifier, including: a body; first to third accommodation portions configured to have respective open top surfaces in order to separately accommodate a battery, an air compressor, and water inside the body; first to third covers configured to selectively open and close the respective open top surfaces of the first to third accommodation portions; an air inlet formed in the bottom surface of the body, connected to the lower portion of the second accommodation portion via a path, and configured to accommodate a pre-filter; a siphon pipe positioned upright inside the water of the third accommodation portion, and configured such that the top thereof is connected to the air outlet of the air compressor; a cannula installed on the top of the third accommodation portion, and configured to supply purified, humidified air to a user; and a power switch installed on one side of a side surface of the body, and configured to control the amount of air to be supplied while selectively turning on and off the driving of the air compressor.

A charging adaptor connector may be installed on one side of the side surface of the body in order to charge the battery.

A belt hook may be formed on one side of the rear surface of the body.

First and second flanges may be installed at the center of the second cover and on one side of the third cover, respectively, in order to connect the air outlet of the air compressor and the top of the siphon pipe via a connection hose, and a third flange may be installed on the other side of the third cover in order to connect with the cannula.

A cover mesh member, hinged such that it is selectively opened and closed to allow the pre-filter to be replaced and cleaned and configured to suck the external air, may be installed in the opening of the air inlet.

A diffuser may be installed at the lower end of the siphon pipe.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
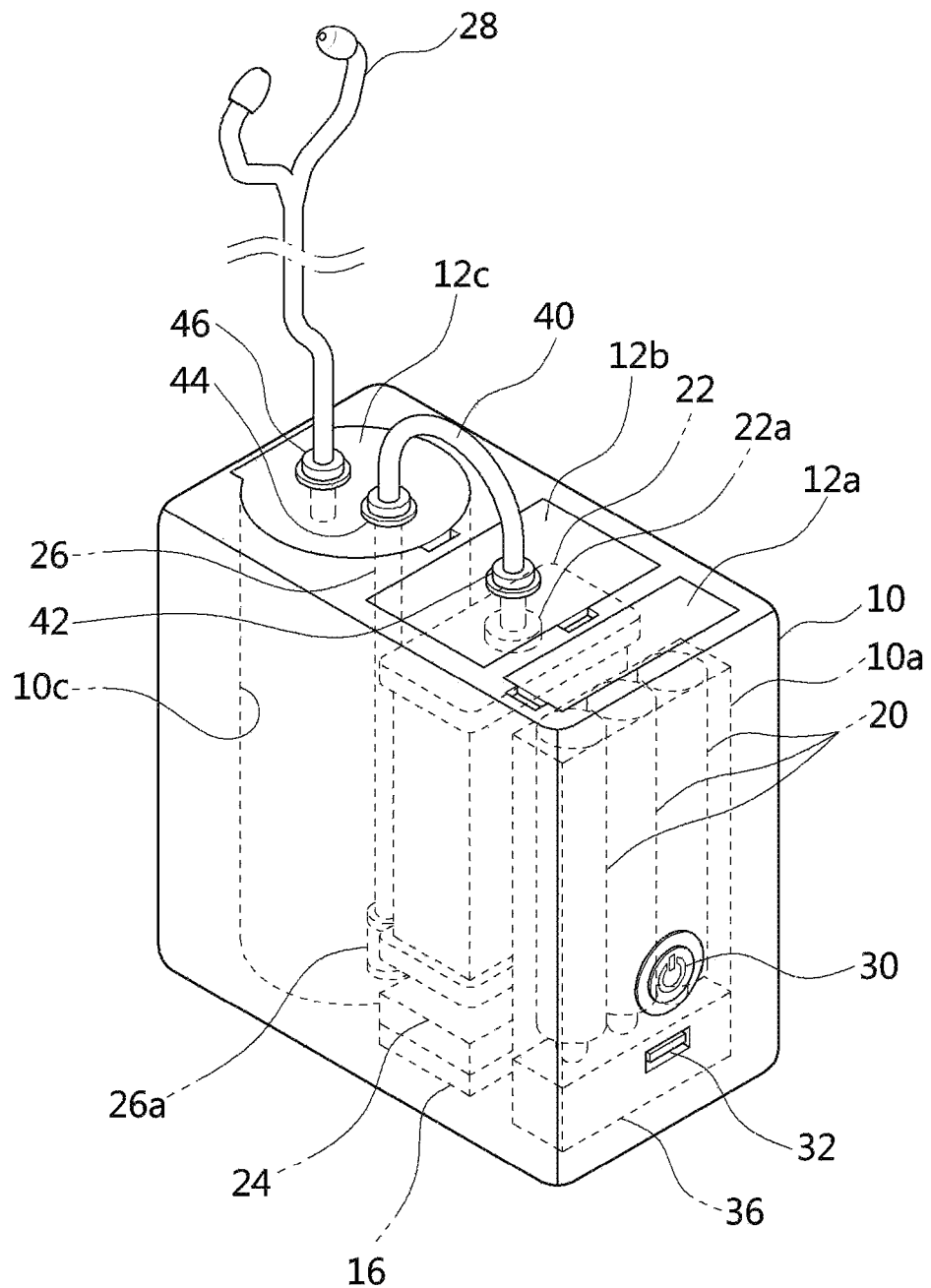
FIG. 1 is a front perspective view showing a portable air purifier according to the present invention.
Figure 2:
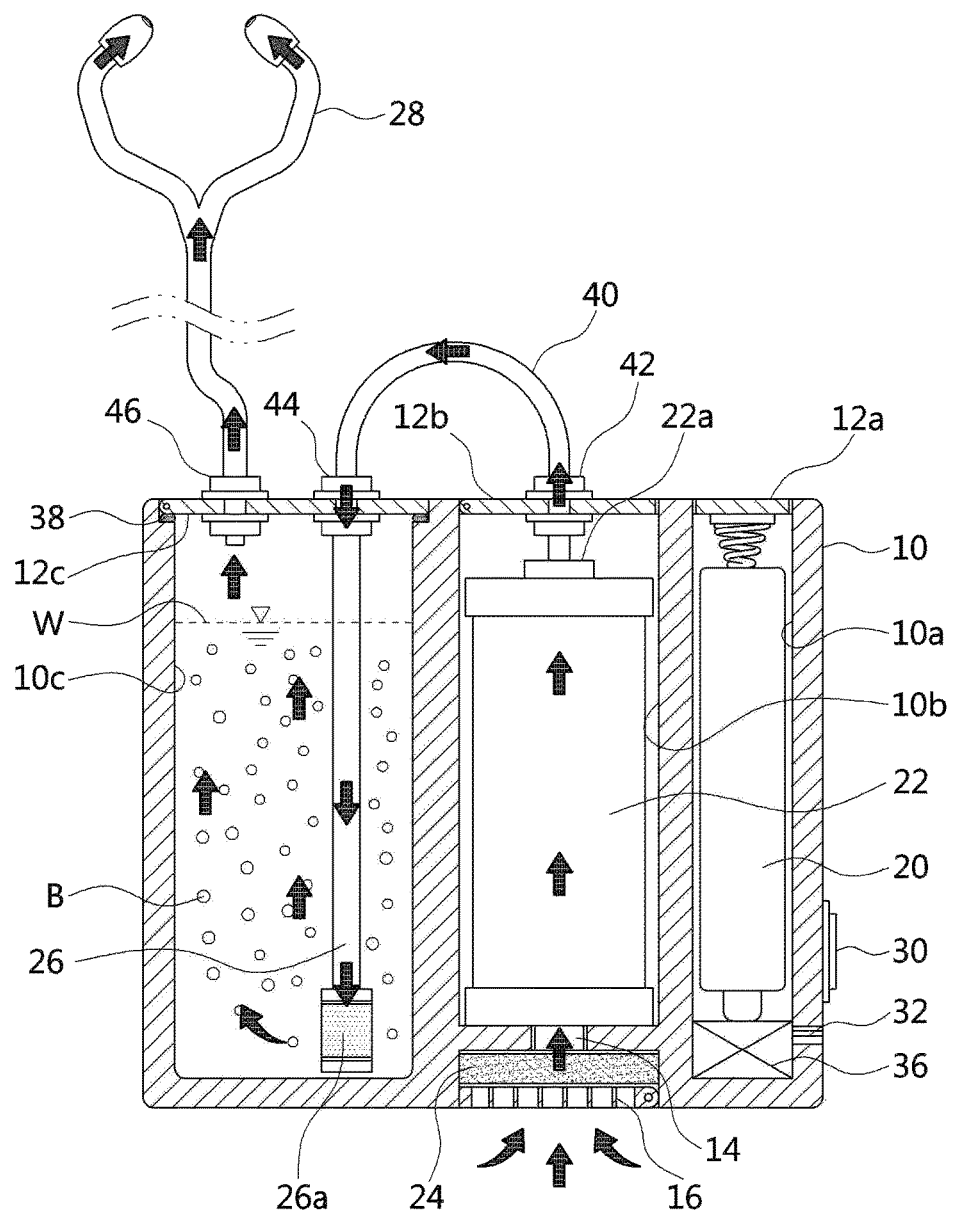
FIG. 2 is a longitudinal section showing the portable air purifier according to the present invention.
Figure 3:
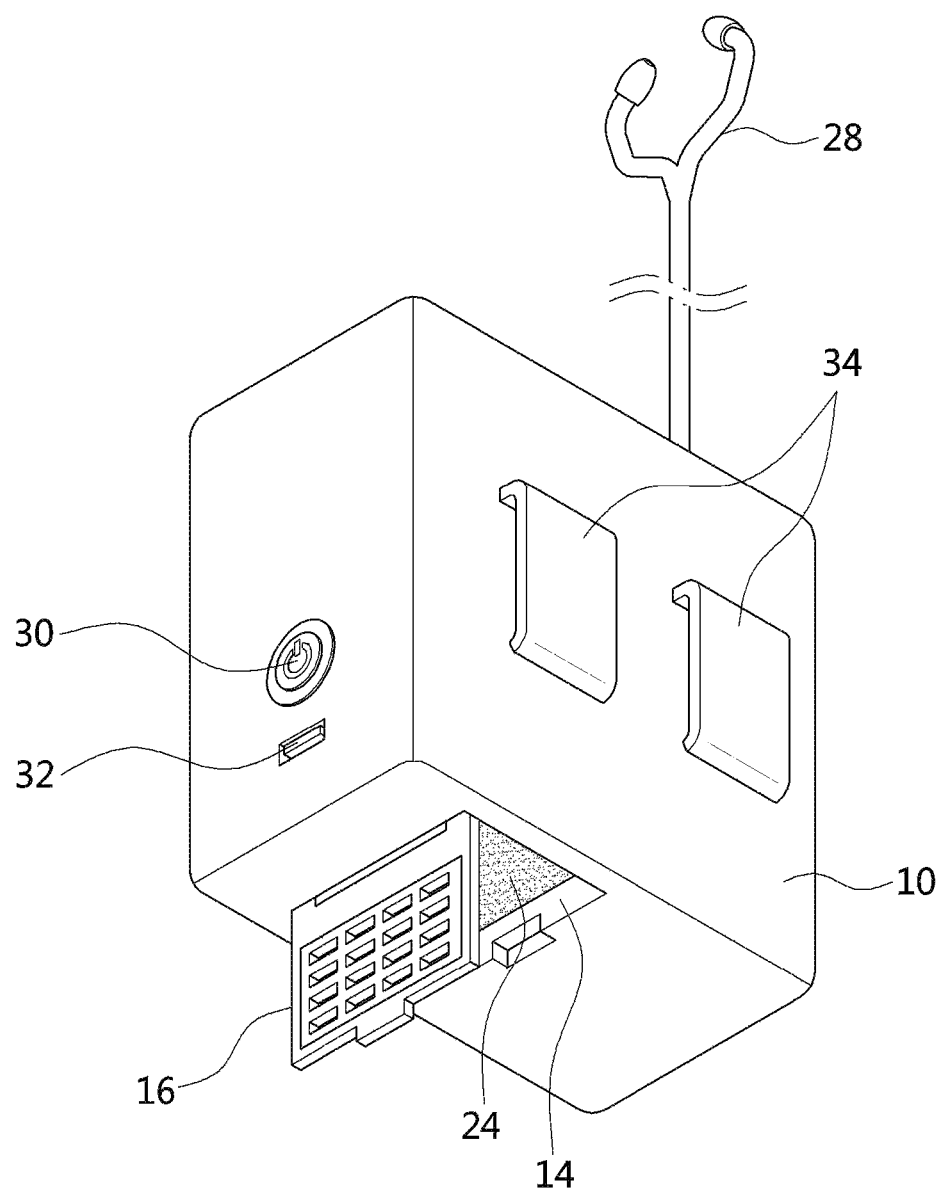
FIG. 3 is a rear perspective view showing the portable air purifier according to the present invention.

An embodiment of the present invention will be described in detail below with reference to FIGS. 1 to 3.

A portable air purifier according to the present invention comprises: a body 10; first to third accommodation portions 10a, 10b, and 10c configured to have respective open top surfaces to separately accommodate a battery 20, an air compressor 22, and water W inside the body 10; first to third covers 12a, 12b, and 12c configured to selectively open and close the respective open top surfaces of the first to third accommodation portions 10a, 10b, and 10c; an air inlet 14 formed in the bottom surface of the body 10, connected to the lower portion of the second accommodation portion 10b via a path, and configured to accommodate a pre-filter 24; a siphon pipe 26 positioned upright in the water W of the third accommodation portion 10c, and configured such that the top thereof is connected to the air outlet 22a of the air compressor 22 and a diffuser 26a is installed at the lower end thereof; a cannula 28 installed on the top of the third accommodation portion 10c, and configured to supply purified, humidified air to a user; and a power switch 30 installed on one side of a side surface of the body 10, and configured to control the amount of air to be supplied while selectively turning on and off the driving of the air compressor 22.

In other words, a charging adaptor connector 32 is installed on one side of the side surface of the body 10 near the power switch 30 in order to charge the battery 20, and belt hooks 34 are formed on one side of the rear surface of the body 10 in order to enable body 10 to be worn on a user via a belt (not shown).

A control box 36 is installed on the bottom of the inside of the first accommodation portion 10a in order to electrically connect to and control the battery 20, the air compressor 22, the power switch 30, and the charging adaptor connector 32.

The first to third covers 12a, 12b, and 12c are configured such that one side of each thereof is hinged to one side of the body 10 and the other side of each thereof is provided with a locking button (not shown) so that the other side is selectively coupled to and separated from the body 10 in order to selectively open and close the first to third accommodation portions 10a, 10b and 10c in a hinged manner.

The third cover 12c is provided with an O ring 38 so that the water W stored inside the third cover 12c does not leak when the open top surface of the third accommodation portion 10c is covered with the third cover 12c.

First and second flanges 42 and 44 are installed at the center of the second cover 12b and on one side of the third cover 12c, respectively, in order to connect the air outlet 22a of the air compressor 22 and the top of the siphon pipe 26 via a connection hose 40, and a third flange 46 is installed on the other side of the third cover 12c in order to connect with the cannula 28.

A cover mesh member 16, hinged such that it is selectively opened and closed to allow the pre-filter 24 to be replaced and cleaned and configured to suck the external air, is installed in the opening of the air inlet 14.

Although the battery 20 may be preferably rechargeable, it may be disposable.

The pre-filter 24 is preferably made of sponge that can be continuously used and can be washed with water.

The cannula 28 may be directly worn in the nasal cavity or oral cavity, or may be connected to and used in connection with a mask.

Next, the operations and effects of the above-described portable air purifier according to the present invention are described in detail below.

In order to use the portable air purifier according to the present invention, when the third accommodation portion 10c is filled with the water W to a predetermined level and the power switch 30 installed on the side surface of the body 10 is pressed, a signal controlled via the control box 36 drives the air compressor 22. Accordingly, a contaminant included in external air is primarily filtered out while the external air is passing through the pre-filter 24 via the cover mesh member 16, and the filtered air is compressed via the air compressor 22 and flows into the siphon pipe 26 via the connection hose 40 connected to the upper air outlet 22a of the air compressor 22.

In this case, the air passing through the siphon pipe 26 forms fine bubbles B while diffusing through the water W filling the third accommodation portion 10c via the diffuser 26a installed on the bottom of the siphon pipe 26. While these bubbles B are slowly floating to the surface of the water W and are bursting, ultra-fine dust included in the air is secondarily separated.

In other words, the ultra-fine dust included in the air is separated from the air and floats in the water W, and purified, humidified air, from which the ultra-fine dust has been separated, is discharged to the outside via the cannula 28 connected to the third cover 12c via the third flange 44. Accordingly, a user can inhale the purified, humidified air by bringing the cannula 28 close to the nasal cavity or oral cavity.

In this case, the body 10 may be worn around the waist of a user by means of the belt hooks 34 formed on the back of the body 10. The user may conveniently carry the portable air purifier regardless of place in preparation for atmospheric pollution, yellow dust, fine dust, etc., thus continuously inhaling purified, humidified air.

Accordingly, according to the present invention, a primary contaminant is filtered out by the pre-filter 24 while external air is being sucked by the air compressor 22, and ultra-fine dust included in the air is secondarily separated by injecting the filtered, compressed air into the water W by means of the siphon pipe 26 and the diffuser 26a, thereby supplying final purified, humidified air into the nasal cavity or oral cavity of a user via the cannula 28. Accordingly, maintenance costs required for the periodic replacement of a special filter unit can be eliminated, manufacturing costs can be reduced by minimizing internal components and thus reducing the volume of the portable air purifier, and the carrying of the portable air purifier can be facilitated.

Meanwhile, the present invention is not limited only to the above-described embodiment. It will be apparent to those skilled in the art that modifications and variations can be made without departing from the gist of the present invention and technical spirit related to such modifications and variations should be construed as falling within the claims.

What is claimed is:

1. A portable air purifier, comprising:
   a body comprising a top surface, a bottom surface and side surfaces;
   first, second, and third accommodation portions of the body configured to have respective open, adjacent top surfaces on the top surface of the body and separately accommodating a battery, an air compressor, and water inside the body;
   first, second, and third covers configured to selectively open and close the respective open, adjacent top surfaces of the first, second, and third accommodation portions;
   an air inlet formed in the bottom surface of the body, connected to a lower portion of the second accommodation portion via a path, and configured to accommodate a pre-filter;

a siphon pipe positioned upright inside the water of the third accommodation portion, and configured such that a top of the siphon pipe is connected to an air outlet of the air compressor;

a cannula installed on the third cover of the third accommodation portion, and configured to supply purified, humidified air to a user;

a power switch installed on one side of a first side surface of the body, and configured to control an amount of air to be supplied while selectively turning on and off driving of the air compressor;

a belt hook formed on one side of a second side surface of the body;

first and second flanges installed at a center of the second cover and on one side of the third cover, respectively, in order to connect the air outlet of the air compressor and the top of the siphon pipe via a connection hose, and a third flange installed on a remaining side of the third cover in order to connect with the cannula; and a diffuser installed at a lower end of the siphon pipe, wherein the air compressor is configured to compress air so that, in use, compressed air passing through the siphon pipe forms bubbles while diffusing through the water via the diffuser, whereby ultra-fine dust included in the air is separated from the air through the generation of the bubbles in the water and bursting of the bubbles, and then the purified and humidified air is supplied to the user via the cannula.

2. The portable air purifier of claim 1, further comprising a charging adaptor connector installed on one side of the first side surface of the body in order to charge the battery.

3. The portable air purifier of claim 1, further comprising a cover mesh member, hinged such that it is selectively openable and closable to allow the pre-filter to be replaced and cleaned and configured to pass the external air therethrough, the cover mesh member being installed in an opening of the air inlet.

* * * * *